(12) United States Patent
Ertl et al.

(10) Patent No.: US 11,339,415 B2
(45) Date of Patent: *May 24, 2022

(54) PROCESS FOR THE ENZYMATIC REGENERATION OF REDOX COFACTORS

(71) Applicant: ANNIKKI GMBH, Graz (AT)

(72) Inventors: Ortwin Ertl, Vasoldsberg (AT); Nicole Staunig, Vasoldsberg (AT); Marta Sut, Graz (AT); Bernd Mayer, Graz (AT)

(73) Assignee: ANNIKKI GMBH, Graz (AT)

( * ) Notice: Subject to any disclaimer, the term of this patent is extended or adjusted under 35 U.S.C. 154(b) by 212 days.

This patent is subject to a terminal disclaimer.

(21) Appl. No.: 16/451,838

(22) Filed: Jun. 25, 2019

(65) Prior Publication Data

US 2019/0323051 A1   Oct. 24, 2019

Related U.S. Application Data

(60) Continuation of application No. 15/490,416, filed on Apr. 18, 2017, now Pat. No. 10,370,691, which is a division of application No. 14/376,512, filed as application No. PCT/EP2013/052313 on Feb. 6, 2013, now Pat. No. 9,644,227.

(30) Foreign Application Priority Data

Feb. 7, 2012   (EP) ........................ 2450007
Sep. 12, 2012  (WO) ............... PCT/IB2012/067781
Dec. 10, 2012  (AT) ............... A 1284/2012

(51) Int. Cl.
| | |
|---|---|
| *C12P 41/00* | (2006.01) |
| *C12P 19/02* | (2006.01) |
| *C12P 33/00* | (2006.01) |
| *C12P 19/36* | (2006.01) |

(52) U.S. Cl.
CPC ............ *C12P 41/002* (2013.01); *C12P 19/02* (2013.01); *C12P 19/36* (2013.01); *C12P 33/00* (2013.01)

(58) Field of Classification Search
None
See application file for complete search history.

(56) References Cited

U.S. PATENT DOCUMENTS

| | | | |
|---|---|---|---|
| 7,163,815 B2 | 1/2007 | Riebel-Bommarius et al. | |
| 9,644,227 B2 | 5/2017 | Ertl et al. | |
| 2009/0280525 A1 | 11/2009 | Gupta et al. | |
| 2012/0003688 A1 | 1/2012 | Bommarius et al. | |

FOREIGN PATENT DOCUMENTS

| | | |
|---|---|---|
| EP | 1285962 | 2/2003 |
| EP | 1731618 | 12/2006 |
| EP | 1925674 | 5/2008 |
| WO | WO 86/04353 | 7/1986 |
| WO | WO2004/022764 | 3/2004 |
| WO | WO2007/118644 | 10/2007 |
| WO | WO2009/121785 | 10/2009 |
| WO | WO2011/000693 | 1/2011 |
| WO | WO2013/117251 | 8/2013 |

OTHER PUBLICATIONS

Applied Microbiology and Biotechnology, "Identification, cloning, heterologous expression, and characterization of a NADPH-dependent 7β-hydroxysteroid dehydrogenase from *Collinsella aerofaciens*", 2011 vol. 90 p. 127-135.
Hummel et al., "An Efficient and Selective Enzymatic Oxidation System for the Synthesis of Enantiomerically Pure D-tert-Leucine", Organic Letters, 2003, vol. 5, p. 3649-3650.
Findrick et al., "Coenzyme regeneration catalysed by NADH oxidase from *Lactobacillus brevis* in the reaction of L-amino acid oxidation", Biochemical Engineering Journal, 2008, vol. 39(2) p. 319-327.
Monti et al: "One-pot Multienzymatic Synthesis of 12-Ketoursodeoxycholic Acid: Subtle Cofactor Specificities Rule the Reaction Equilibria of Five Biocatalysts Working in a Row", Advanced Synthesis and Catalysis, Wiley-VCH Verlag, Weinheim, vol. 351, No. 9, Jun. 1, 2009, p. 1303-1311.
Schrittwieser et al: "Recent biocatalytic oxidationreduction cascades", Current Opinion in Chemical Biology, vol. 15, No. 2, Apr. 11, p. 249-256, XP028187359.
Suye et al: "Enzymatic production of 1-alanine from malic acid with malic enzyme and alanine dehydrogenase with coenzyme regeneration", The Canadian Journal of Chemical Engineering, vol. 70, No. 2, Apr. 1, 1992, p. 306-312.
Voss et al: "Orchestration of Concurrent Oxidation and ReductionCycles for Stereoinversion and Deracemisation of sec-Alcohols", Journal of the American Chemical Society, vol. 130, No. 42, Oct. 22, 2008, p. 13969-1397.
Woodyer et al: "Mechanistic investigation of a highly active phosphite dehydrogenase mutant and its application for NADPH regeneration", FEBS Journal, vol. 272, No. 15, Aug. 1, 2005, p. 3816-3827.
International Preliminary Report on Patentability for PCT Application No. PCT/EP2013/052313 dated Aug. 12, 2014 (14 pgs).

(Continued)

*Primary Examiner* — Michelle F. Paguio Frising
(74) *Attorney, Agent, or Firm* — Workman Nydegger

(57) ABSTRACT

A process for the enzymatic regeneration of the redox cofactors $NAD^+/NADH$ and $NADP^+/NADPH$ in a one-pot reaction, wherein, as a result of at least two further enzymatically catalyzed redox reactions proceeding in the same reaction batch (product-forming reactions), one of the two redox cofactors accumulates in its reduced form and, respectively, the other one in its oxidized form, characterized in that a) in the regeneration reaction which reconverts the reduced cofactor into its original oxidized form, oxygen or a compound of general formula $R_1C(O)COOH$ is reduced, and b) in the regeneration reaction which reconverts the oxidized cofactor into its original reduced form, a compound of general formula $R_2CH(OH)R_3$ is oxidized and wherein $R_1$, $R_2$ and $R_3$ in the compounds have different meanings.

17 Claims, 11 Drawing Sheets

(56) References Cited

OTHER PUBLICATIONS

U.S. Appl. No. 15/490,416, Nov. 2, 2018, Office Action.
U.S. Appl. No. 15/490,416, Apr. 1, 2019, Notice of Allowance.
Frenette et al., "Polyol Pathway in Human Epididymis and Semen", Journal of Andrology 2006, vol. 27, pp. 233-239.

PROCESS FOR THE ENZYMATIC REGENERATION OF REDOX COFACTORS

CROSS REFERENCE TO RELATED APPLICATIONS

This Application is a continuation of U.S. patent application Ser. No. 15/490,416, filed Apr. 18, 2017, which is a division of U.S. patent application Ser. No. 14/376,512, filed Aug. 4, 2014, issued U.S. Pat. No. 9,644,227, which is a 371 application of PCT/EP2013/052313, filed Feb. 6, 2013, which claims the benefit of European Patent Application No. 2450007.5, filed Feb. 7, 2012, International Patent Application No. PCT/IB2012/067781, filed Sep. 12, 2012, and Austrian Patent Application No. 1284/2012, filed Dec. 10, 2012. The disclosures of the foregoing are incorporated by reference in their entirety.

BACKGROUND OF THE INVENTION

The present invention relates to a process for the enzymatic regeneration of the redox cofactors $NAD^+/NADH$ and $NADP^+/NADPH$ in a one-pot reaction, wherein, as a result of at least two further enzymatically catalyzed redox reactions proceeding in the same reaction batch (=product-forming reactions), one of the two redox cofactors accumulates in its reduced form and, respectively, the other one in its oxidized form.

PRIOR ART

Enzymatically catalyzed redox reactions are used in industrial operations, for example, in the production of chiral alcohols, α-amino acids and α-hydroxy acids. The majority of enzymes employed in industrial redox reactions use cofactors such as NADH or NADPH. Among enzymatic redox reactions, those are particularly interesting wherein redox cofactors are restored by in situ cofactor regeneration systems. The reason therefor is that it is possible to use only catalytic amounts of the expensive cofactors $(NAD(P)^+/NAD(P)H)$. The availability of suitable dehydrogenases and other enzymes has resulted in the development of various cofactor regeneration systems.

The regeneration systems described up to now may be classified as: enzyme-linked, substrate-linked, in vivo (natural cofactor regeneration systems in living organisms), photochemical, chemical or electro-enzymatic. The process herein described relates to an enzyme-linked regeneration system. Advantages of enzyme-linked systems are high selectivity, applicability for the production of various products and a high reuse rate of the cofactor (total turnover number, TTN).

In the mid-90ies, a first industrial process using an enzyme-linked cofactor regeneration system was employed on a ton scale. In said process, formate dehydrogenase from *Candida boidinii* was used. The industrial processes yet known normally use a redox enzyme for the synthesis of the product and a further enzyme for the cofactor regeneration.

Processes wherein two or more enzymatic redox reactions which are involved in the formation of the product and two enzymatic systems for the cofactor regeneration (simultaneously or sequentially) are proceeding in one reaction batch without an intermediate being isolated must be distinguished therefrom. Recently, such enzymatic cascade reactions— herein referred to as one-pot reactions—have drawn significant attention, since they effectively reduce operating costs, operating time and environmental impacts. In addition, enzymatic cascades of redox reactions facilitate transformations which are not easy to implement by conventional chemical methods.

It is, however, a challenge to perform several reactions (oxidation and reduction) simultaneously in one one-pot reaction with a parallel cofactor regeneration, since highly divergent reaction conditions are often required for the individual transformations. So far, only a very small number of one-pot trials comprising oxidation and reduction reactions with associated cofactor regeneration systems have been performed.

In the literature (Advanced Synth. Catal., 2008, Volume 351, Issue 9, p. 1303-1311), the experiment of a one-pot reaction using 7α-hydroxysteroid dehydrogenase (HSDH), 7β-HSDH and 12α-HSDH has been described. In said process, an oxidation, both regioselective and stereoselective, was performed at positions 7 and 12 of cholic acid, followed by a regio- and stereoselective reduction at position 7. In that process both, a lactate dehydrogenase ($NAD^+$-dependent) and a glucose dehydrogenase ($NADP^+$-dependent) were used as a cofactor regeneration system. Pyruvate and glucose were used as cosubtrates. Although this process was originally aimed at a true one-pot process, at the end oxidation and reduction reactions were performed separately. In doing so, the partitioning of oxidative and reductive steps occurred either in a so-called "tea bag"-reactor or in a membrane reactor. Said partitioning was necessary in order to avoid the production of byproducts due to the low cofactor selectivity of NADPH-glucose dehydrogenase. However, in the one-pot reaction, the glucose dehydrogenase $NADP^+$ converted partly also $NAD^+$, which impeded the oxidation. In the process described, only 12.5 mM (~0.5%) of the substrate cholic acid was used, which renders the process uninteresting from an ecological point of view.

Furthermore, an attempt to perform the deracemization of racemates of secondary alcohols via a prochiral ketone as an intermediate using a one-pot system has been described (J. Am. Chem. Soc., 2008, Volume 130, p. 13969-13972). The deracemization of secondary alcohols was achieved via two alcohol dehydrogenases (S- and R-specific) with different cofactor specificities. In said system, NADP was regenerated by NADPH oxidase (hydrogen peroxide producing) and NADH was regenerated by formate dehydrogenase. Formate and oxygen were used as cosubstrates. In that system 4 enzymes were used without partitioning of oxidative and reductive steps. A drawback of the process is the very low concentration of the substrate used of 0.2-0.5%, which is inappropriate for industrial purposes.

A further one-pot system has been described in WO 2009/121785 A2. In said process, a stereoisomer of an optically active secondary alcohol was oxidized to the ketone and then reduced to the corresponding optical antipode, wherein two alcohol dehydrogenases having opposite stereoselectivities and different cofactor specificities were used. The cofactors were regenerated by means of a so-called "hydride-transfer system", using only one additional enzyme. For regenerating the cofactors, various enzymes such as formate dehydrogenase, glucose dehydrogenase, lactate dehydrogenase were used. A drawback of said process is the low concentration of the substrates used.

A drawback of the enzymatic one-pot methods involving cofactor regeneration systems yet known is altogether the very low substrate concentration, which is inefficient for industrial processes.

In contrast to that, many individual enzymatic redox reactions are already known in which cofactor regeneration systems are used. The experiments were described with whole microorganisms, cell lysates or isolated enzymes with concurrent NAD(P)H or NAD(P)$^+$ regeneration. Known enzymatic cofactor regeneration systems for individual redox reactions comprise, for example, formate dehydrogenase for NADH (formate as a cosubstrate), alcohol dehydrogenase from *Pseudomonas* sp. for NADH (2-propanol as a cosubstrate), hydrogenase for NADH and NADPH ($H_2$ as a cosubstrate), glucose-6-phosphate dehydrogenase from *L. mesenteroides* for NADPH (glucose-6-phosphate as a cosubstrate), glucose dehydrogenase for NADH and NADPH (glucose as a cosubstrate), NADH oxidase for NADH ($O_2$ as a cosubstrate) and phosphite dehydrogenase for NADH (phosphite as a cosubstrate).

An example of use of such individual redox reactions is the production of chiral hydroxy compounds, starting from appropriate prochiral keto compounds. In said process, the cofactor is regenerated by means of an additional enzyme. These methods have in common that they constitute an isolated reduction reaction and regenerate NAD(P)H (see e.g. EP 1 152 054).

Enzymatic processes using hydroxysteroid dehydrogenases, coupled with a cofactor regeneration system, which proceed at higher substrate concentrations (approx. >1%), have been described (EP 1 731 618; WO 2007/118644; Appl. Microbiol. Biotechnol., 2011 Volume 90 p. 127-135). In said processes, the cofactors NAD(P)H or NAD(P) were regenerated by means of different enzymes such as, e.g., lactate dehydrogenase (pyruvate as a cosubstrate), alcohol dehydrogenase from *T. brockii* (isopropanol als as a cosubstrate), alcohol dehydrogenase from *L. brevis, L. minor, Leuconostoc carnosum, T. ethanolicus, Clostridium beijerinckii*. However, these known processes relate merely to the isolated single reactions for the oxidation of a hydroxy compound or for the reduction of an oxo compound.

A cofactor regeneration system for NADH using malate dehydrogenase ("malate enzyme") has already been described (Can. J. Chem. Eng. 1992, Volume 70, p. 306-312). In said publication, it was used for the reductive amination of pyruvate by alanine dehydrogenase. The pyruvate emerging during the cofactor regeneration was subsequently used in the product-forming reaction.

In WO 2004/022764, it is likewise described to regenerate NADH by malate dehydrogenase. Differently to the previously described publication the pyruvate emerging during the oxidative decarboxylation of malate was not used further.

An example of an enzymatic reduction of D-xylose to xylitol involving a cofactor regeneration system has been described (FEBS J., 2005, Volume 272, p. 3816-3827). An NADPH-dependent mutant of phosphite dehydrogenase from *Pseudomonas* sp. was used as the cofactor regeneration enzyme. This is also a single reaction for the formation of a product.

Further examples of an enzymatic production of chiral enantiomerically enriched organic compounds, e.g., alcohols or amino acids, have been described (Organic Letters, 2003, Volume 5, p. 3649-3650; U.S. Pat. No. 7,163,815; Biochem. Eng. J., 2008, Volume 39(2) p. 319-327; EP 1 285 962). In said systems, an NAD(P)H-dependent oxidase from *Lactobacillus brevis* or *Lactobacillus sanfranciscensis* was used as the cofactor regeneration enzyme. The trials likewise constitute single reactions for the formation of a product.

In WO 2011/000693, a 17beta-hydroxysteroid dehydrogenase as well as a process are described enabling the execution of redox reactions at position 17 of 4-androstene-3,17-dione. Again, this is an isolated reduction reaction. The above-mentioned individually proceeding oxidation or reduction reactions lack the advantages of a one-pot reaction, such as for example cost-effectiveness as a result of time and material savings as well as a better turnover due to enzymatic cascade reactions.

SUMMARY

The object of the present invention was to provide a process for regenerating the redox cofactors NAD$^+$/NADH and/or, e.g. and, NADP$^+$/NADPH in order to perform therewith two or more enzymatically catalyzed redox reactions in one reaction batch in an economical fashion.

Figure 1:
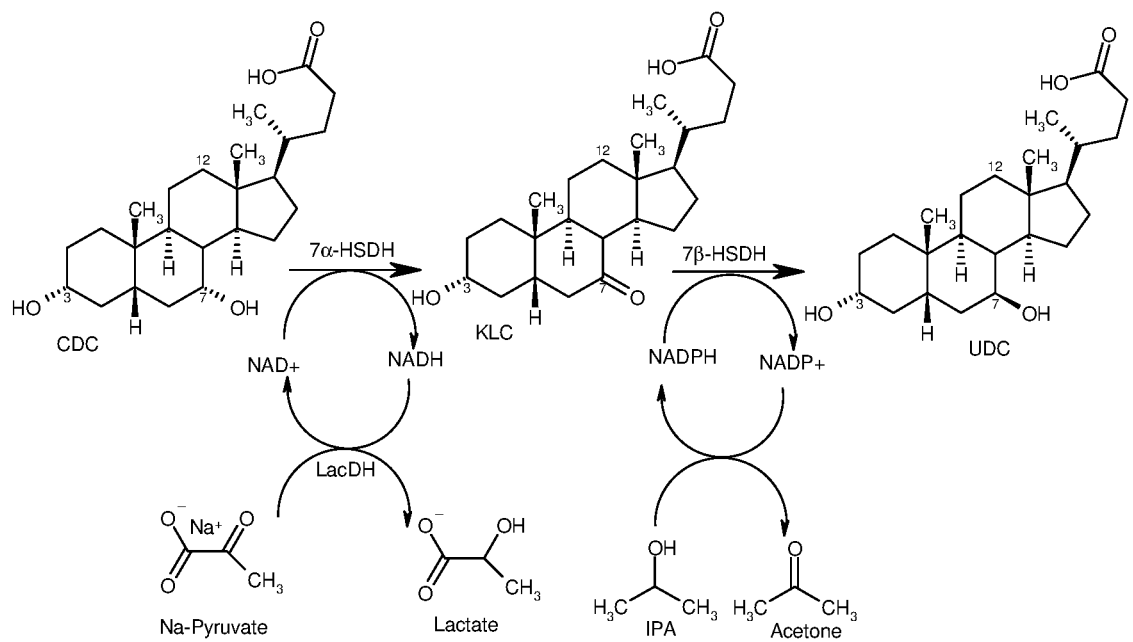
FIG. 1 shows the reaction scheme of the epimerization of chenodeoxycholic acid into ursodeoxycholic acid via the intermediate 3α-hydroxy-7oxo-5β-cholanic acid, with cofactor regeneration using 2-propanol and pyruvate.
Figure 2:
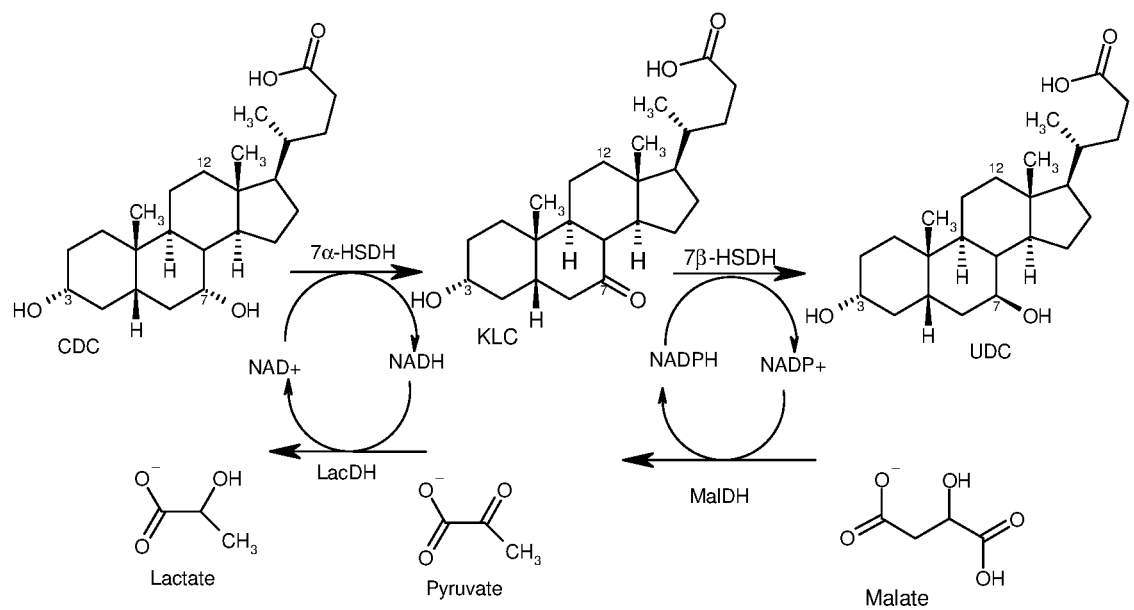
FIG. 2 shows the reaction scheme of the epimerization of chenodeoxycholic acid into ursodeoxycholic acid via the intermediate 3α-hydroxy-7oxo-5β-cholanic acid, with cofactor regeneration using malate and pyruvate.
Figure 3:
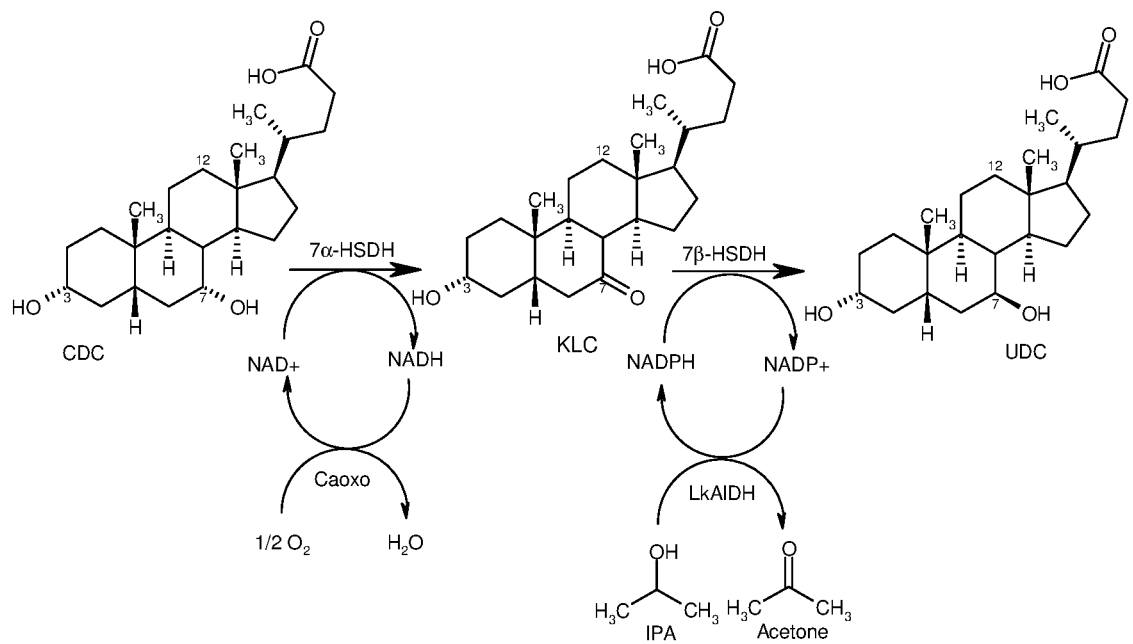
FIG. 3 shows the reaction scheme of the epimerization of chenodeoxycholic acid into ursodeoxycholic acid via the intermediate 3α-hydroxy-7oxo-5β-cholanic acid, with cofactor regeneration using 2-propanol and oxygen.
Figure 4:
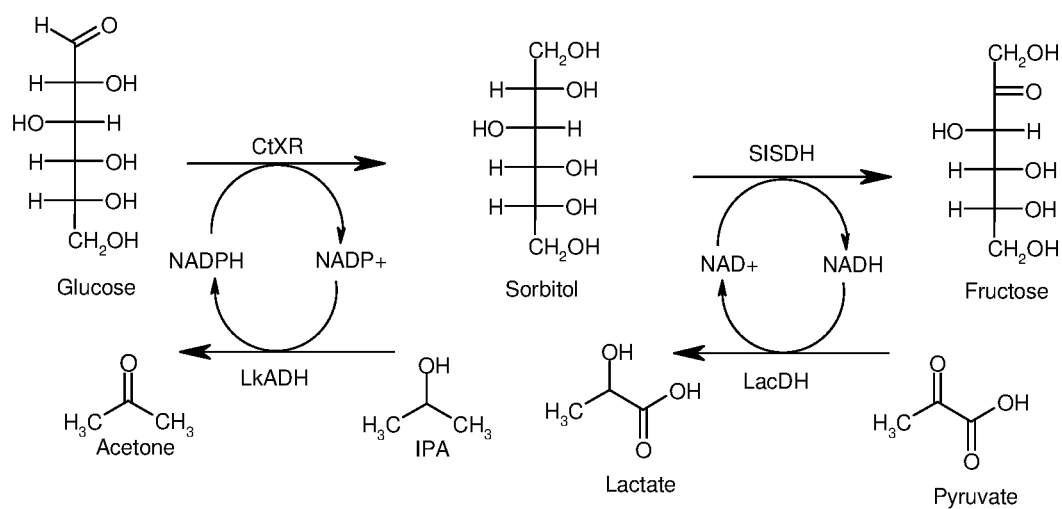
FIG. 4 shows the reaction scheme of the isomerization of glucose into fructose, with cofactor regeneration using 2-propanol and pyruvate.
Figure 5:
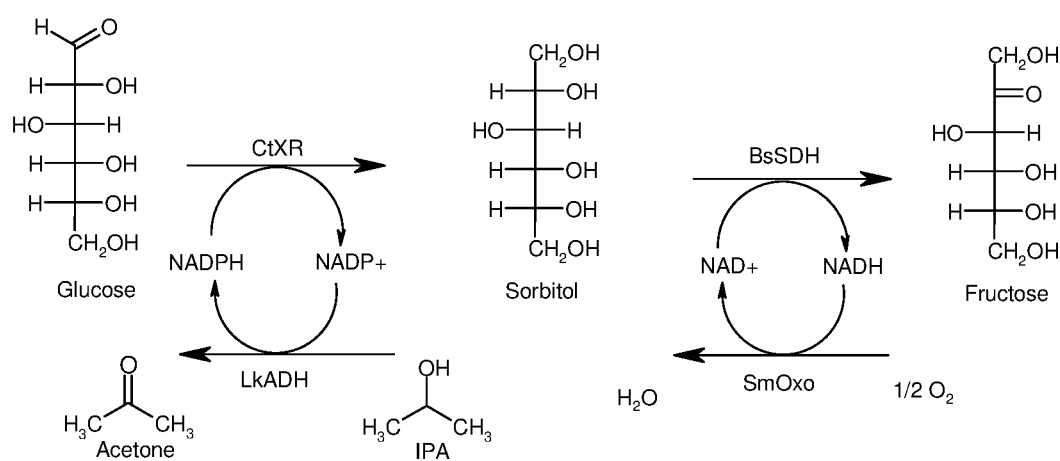
FIG. 5 shows the reaction scheme of the isomerization of glucose into fructose, with cofactor regeneration using 2-propanol and oxygen.
Figure 6:
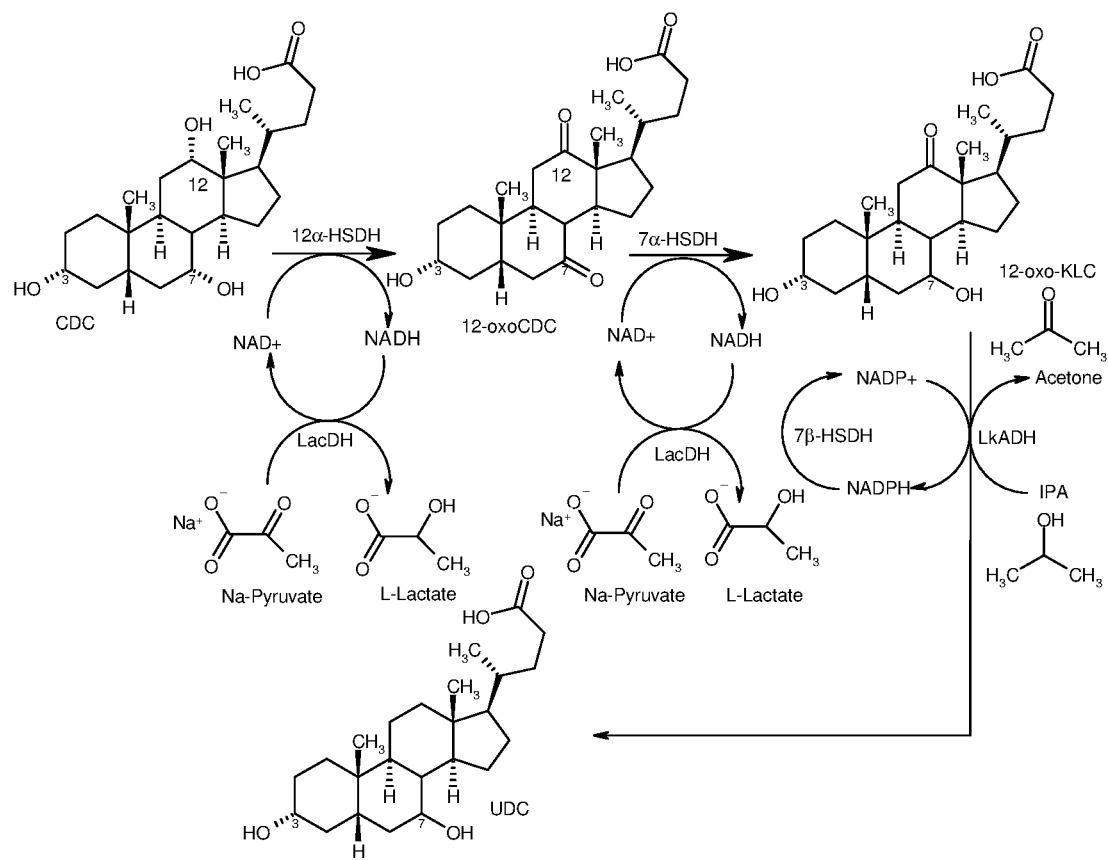
FIG. 6 shows the reaction scheme of the epimerization of cholanic acid to 3α,7β-dihydroxy-12-oxo-5β-cholanic acid via the intermediates 3α,7α-dihydroxy-12-oxo-5β-cholanic acid and 3α-hydroxy-7,12-dioxo-5β-cholanic acid with cofactor-regeneration using 2-propanol and pyruvate.
Figure 7:
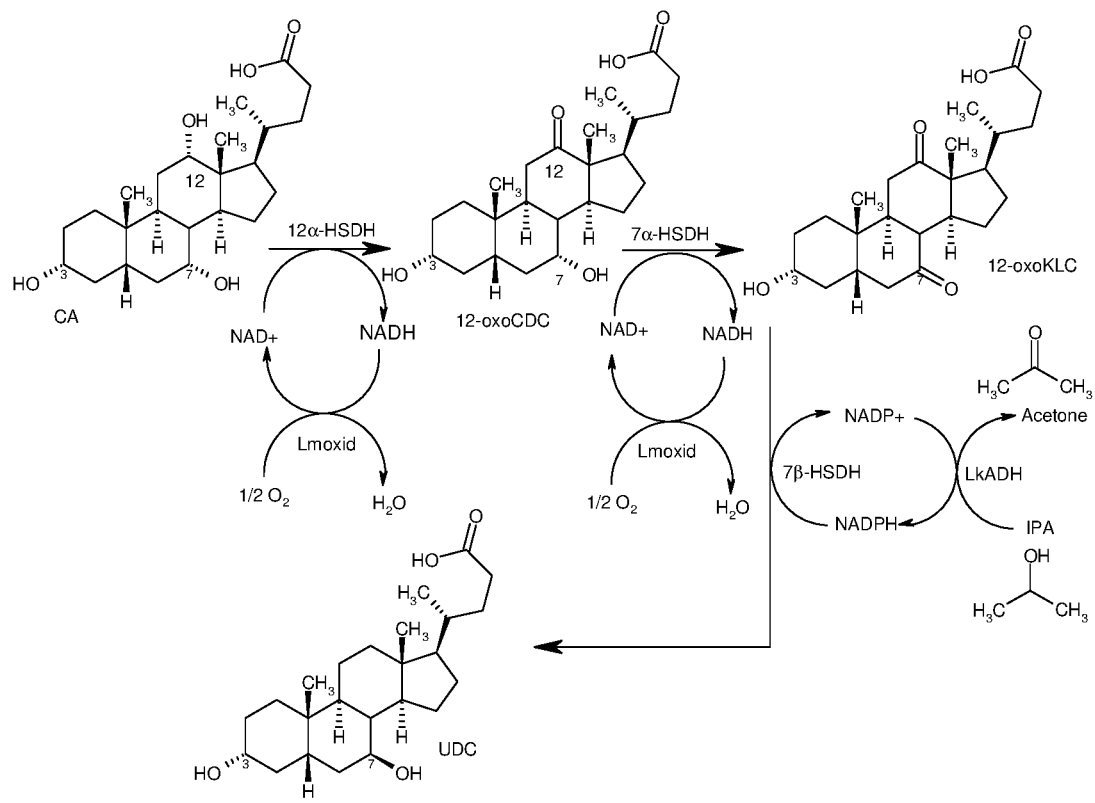
FIG. 7 shows the reaction scheme of the epimerization of cholanic acid to 3α,7β-dihydroxy-12-oxo-5β-cholanic acid via the intermediates 3α,7α-dihydroxy-12-oxo-5β-cholanic acid and 3α-hydroxy-7,12-dioxo-5β-cholanic acid with cofactor-regeneration of the epimerization of cholanic acid to 3α,7β-dihydroxy-12-oxo-5β-cholanic acid via the intermediates 3α,7α-dihydroxy-12-oxo-5β-cholanic acid and 3α-hydroxy-7,12-dioxo-5β-cholanic acid with cofactor-regeneration using 2-propanol and oxygen.
Figure 8:
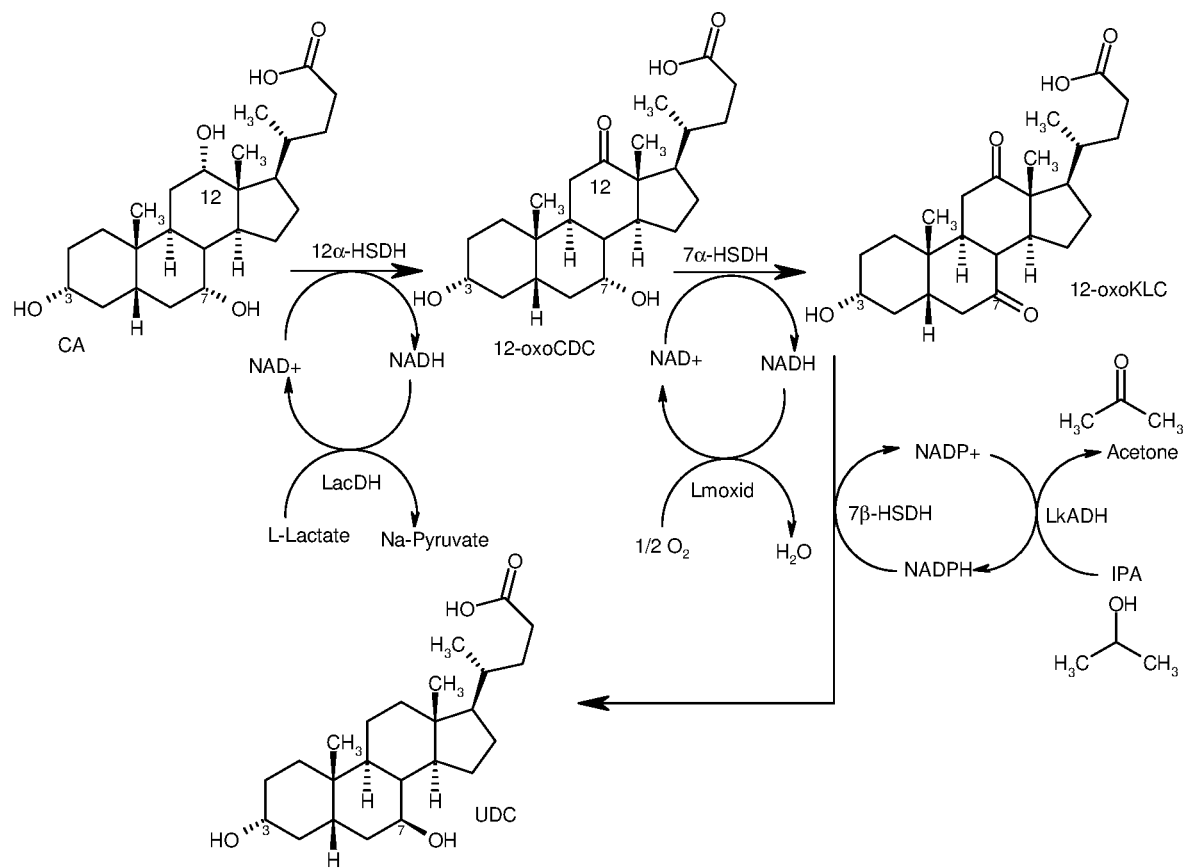
FIG. 8 and FIG. 9 show the reaction schemes of the epimerization of cholanic acid to 3α,7β-dihydroxy-12-oxo-5β-cholanic acid via the intermediates 3α,7α-dihydroxy-12-oxo-5β-cholanic acid and 3α-hydroxy-7,12-dioxo-5β-cholanic acid with cofactor-regeneration using 2-propanol, pyruvate and oxygen.
Figure 9:
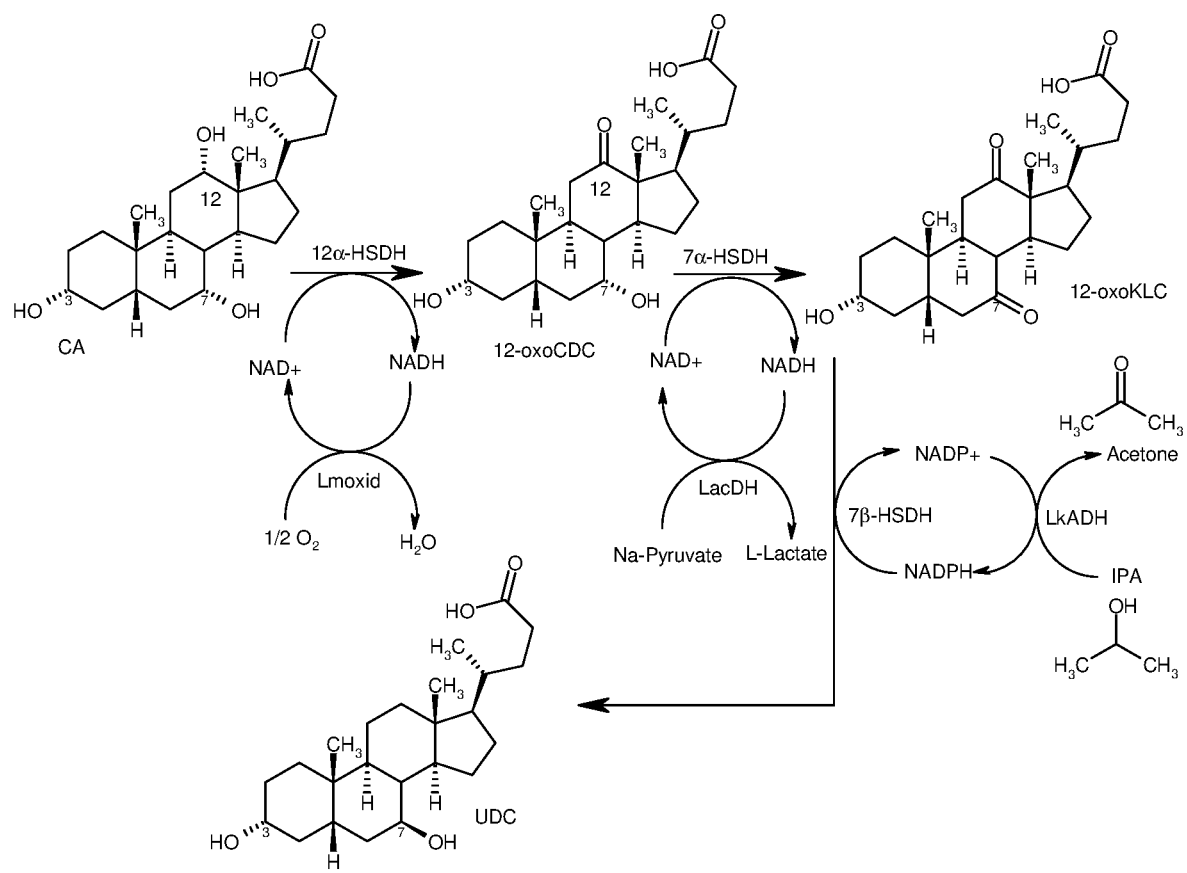
Figure 10:
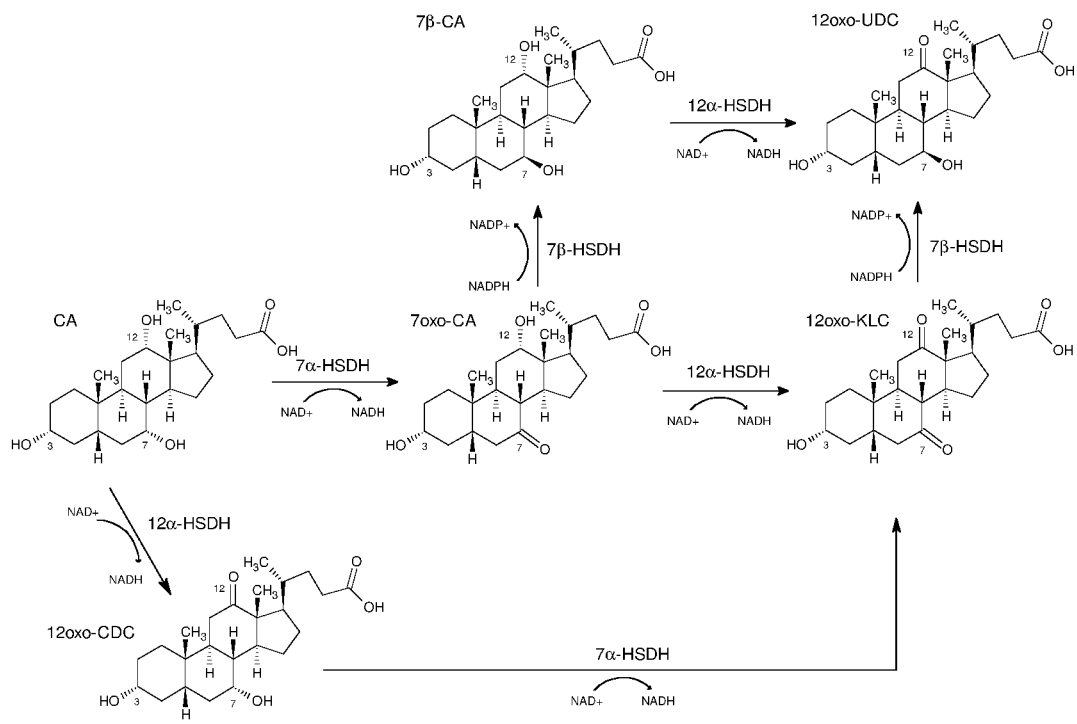
FIG. 10 shows possible reaction schemes of the epimerization of cholanic acid to 3α,7β-dihydroxy-12-oxo-5β-cholanic acid via different intermediates and cofactor-regeneration systems. For regeneration of NAD+ alternatively lactate dehydrogenase (pyruvate as a substrate) and NADH oxidase (oxygen as a substrate) were used. For regeneration of NADPH alcohol dehydrogenase (isopropanol as a substrate) was used.
Figure 10:
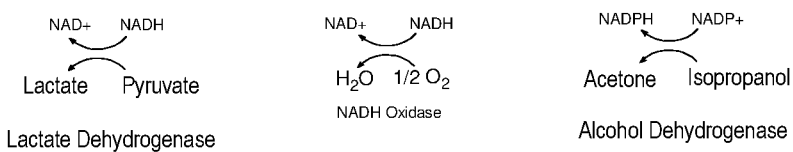
Figure 11:
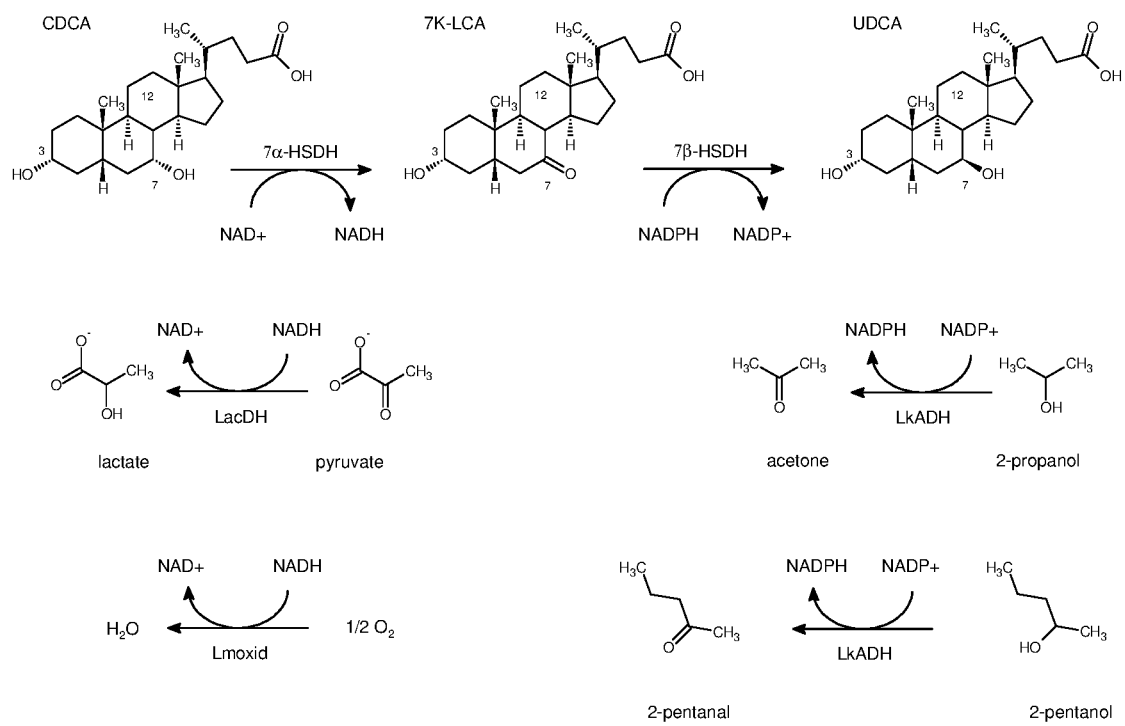
FIG. 11 shows the reaction scheme of the epimerization of chenodeoxycholanic acid to ursodeoxycholanic acid via the intermediate 3α-hydroxy-7oxo-5β-cholanic acid (7-ketolithocholanic acid=7K-LCA=KLC) with cofactor regeneration using 2-propanol and 2-pentanol (in each case alcohol dehydrogenase) as well as pyruvate (lactate dehydrogenase) and oxygen (NADH oxidase).

In the figures the following abbreviations are used:
BsSDH=sorbitol dehydrogenase from *Bacillus subtilis*
CA=3α,7α,12α-trihydroxy-5β-cholanic acid
7β-CA=3α,7β,12α, -trihydroxy-5β-cholanic acid
Caoxo=*Clostridium aminovalericum* NADH oxidase
CDC, CDCA=3α,7α-dihydroxy-5β-cholanic acid
CtXR=*Candida tropicalis* xylose reductase
7α-HSDH=7α-hydroxysteroid dehydrogenase
7β-HSDH=7β-hydroxysteroid dehydrogenase
12α-HSDH=12α-hydroxysteroiddehydrogenase
KLC=3α-hydroxy-7-oxo-5β-cholanic acid
7K-LCA=3α-hydroxy-7-oxo-5β-cholanic acid
LacDH=lacate dehydrogenase NAD(H)-dependent
LkADH=*Lactobacillus kefir* alcohol dehydrogenase NADP(H)-dependent
Lmoxid=*Leuconostoc mesenteroides* NADH-oxidase
MalDH=*E. coli* malate dehydrogenase NADP(H)-dependent
7oxo-CA=3α, 12 α-dihydroxy-7-oxo-5β-cholanic acid
12oxo-CDC=3α,7α-dihydroxy-12-oxo-5β-cholanic acid
12oxo-KLC=3α-hydroxy-7,12-dioxo-5β-cholanic acid
12oxo-UDC=3α,7β-dihydroxy-12-oxo-5β-cholanic acid
SISDH=sheep liver sorbitol dehydrogenase
SmOxo=*Streptococcus mutans* NADH oxidase
UDC. UDCA=3α,7β-dihydroxy-5β-cholanic acid

DETAILED DESCRIPTION

According to the present invention, said object is achieved in a process of the kind initially mentioned, in that a process for the enzymatic regeneration of the redox cofactors NAD$^+$/NADH and/or, e.g. and, NADP$^+$/NADPH in a one-pot reaction is provided, wherein, as a result of at least two further enzymatically catalyzed redox reactions proceeding in the same reaction batch (product-forming reactions), one of the two redox cofactors accumulates in its reduced form and, respectively, the other one in its oxidized form,
which process is characterized in that
a) in the regeneration reaction which reconverts the reduced cofactor into its original oxidized form, oxygen or a compound of general formula

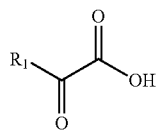

I wherein $R_1$ represents a linear-chain or branched ($C_1$-$C_4$)-alkyl group or a ($C_1$-$C_4$)-carboxy alkyl group, is reduced, and
b) in the regeneration reaction which reconverts the oxidized cofactor into its original reduced form, a ($C_4$-$C_8$)-cycloalcanol or a compound of general formula

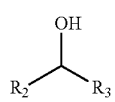

II wherein $R_2$ and $R_3$ are independently selected from the group consisting of H, ($C_1$-$C_6$) alkyl, wherein alkyl is linear-chain or branched, ($C_1$-$C_6$) alkenyl, wherein alkenyl is linear-chain or branched and comprises one to three double bonds, aryl, in particular $C_6$-$C_{12}$ aryl, carboxyl, or ($C_1$-$C_4$) carboxy alkyl, in particular also cycloalkyl, e.g. $C_3$-$C_8$ cycloalkyl,
is oxidized.

A process provided according to the present invention is herein also referred to as "process according to (of) the present invention".

In a further aspect, the present invention provides a process according to the present invention for the enzymatic regeneration of the redox cofactors NAD$^+$/NADH and/or, e.g. and, NADP$^+$/NADPH in a one-pot reaction, wherein, as a result of at least two further enzymatically catalyzed redox reactions proceeding in the same reaction batch (=product-forming reactions), one of the two redox cofactors accumulates in its reduced form and, respectively, the other one in its oxidized form,
which process is characterized in that
a) during the regeneration of the oxidized cofactor, a compound of general formula

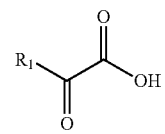

I wherein $R_1$ represents a substituted or unsubstituted $C_1$-$C_4$ alkyl group, is reduced, and
b) during the regeneration of the reduced cofactor, a compound of general formula

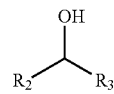

II wherein $R_2$ and $R_3$ independently of each other are selected from the group consisting of
1) —H,
2) —($C_1$-$C_6$) alkyl, wherein alkyl is linear-chain or branched,
3) —($C_1$-$C_6$) alkenyl, wherein alkenyl is linear-chain or branched and optionally comprises up to three double bonds,
4) -cycloalkyl, in particular $C_3$-$C_8$ cycloalkyl,
5) -aryl, in particular $C_6$-$C_{12}$ aryl,
6) —($C_1$-$C_4$) carboxy alkyl, in case compound I is pyruvate, optionally also carboxyl;
is oxidized.

In a further aspect, in a process according to the present invention, $R_2$ and $R_3$ independently of each other are selected from the group consisting of H, ($C_1$-$C_6$) alkyl, wherein alkyl is linear-chain or branched, ($C_1$-$C_6$) alkenyl, wherein alkenyl is linear-chain or branched and comprises one to three double bonds, aryl, in particular $C_6$-$C_{12}$ aryl, carboxyl, or ($C_1$-$C_4$) carboxy alkyl.

Compared to the prior art, a process according to the present invention constitutes a significant improvement of processes in which compounds are both enzymatically oxidized and reduced, since it is enabled to run the required oxidation and reduction reactions as well as the associated reactions for the cofactor regeneration in one reaction batch and, at the same time, to use significantly higher substrate concentrations than according to prior art.

In a process according to the present invention, the cofactors NADH and/or NADPH are used. Therein, $NAD^+$ denotes the oxidized form and NADH denotes the reduced form of nicotinamide adenine dinucleotide, whereas $NADP^+$ denotes the oxidized form and NADPH denotes the reduced form of nicotinamide adenine dinucleotide phosphate.

Enzymatically catalyzed redox reactions which are not part of the cofactor regeneration and, in a process according to the present invention, are involved in the formation of the product are herein referred to as "oxidation reaction(s)" and "reduction reaction(s)". "Oxidation reaction(s)" and "reduction reaction(s)" are summarized under the term "product-forming reactions". The product-forming reactions in a process according to the present invention comprise, in each case, at least one oxidation reaction and at least one reduction reaction.

If $NAD^+$ is used as a cofactor for the oxidation reaction(s), NADPH is the cofactor for the reduction reaction(s). If $NADP^+$ is used as a cofactor for the oxidation reaction(s), NADH is the cofactor for the reduction reaction(s).

In a process according to the present invention, oxidation reaction(s) and reduction reaction(s) can be performed either chronologically parallel or in chronological succession, preferably chronologically parallel in the same reaction batch.

Compounds which are used with the objective of forming a product are herein referred to as substrates. Compounds which are reacted during the cofactor regeneration are herein referred to as cosubstrates.

In a process according to the present invention, one substrate as well as several substrates can be used. In doing so, reduction and/or oxidation reaction(s) can take place on the same substrate (molecular backbone) and also on different substrates, preferably on the same substrate. Furthermore, in a process according to the present invention, reduction and/or oxidation reactions can take place on the same or on different functional groups.

A process according to the present invention is suitable for a plurality of reactions, for example for the inversion of configuration of stereoisomeric hydroxy compounds via oxidation to the corresponding ketone and subsequent reduction to the opposite stereospecific hydroxy compound.

A process in which two or more enzymatic redox reactions involved in the formation of a product and two enzymatic systems for cofactor regeneration proceed in one reaction batch without an intermediate being isolated is herein referred to as a "one-pot reaction".

The mentioning of an acid or a salt of an acid includes herein the respective unmentioned term. Likewise, the mentioning of acids, in particular of bile acids, includes herein all esters derived therefrom. Furthermore, compounds (partly) provided with protective groups are included in the mentioning of the underlying substances.

In a preferred embodiment of the present invention, a process according to the present invention is characterized in that the oxidation reaction and the reduction reaction proceed chronologically parallel.

In a preferred embodiment of the present invention, a process according to the present invention is characterized in that both the oxidation reaction and the reduction reaction occur on the same molecular backbone.

In a preferred embodiment of the present invention, a process according to the present invention is characterized in that, as a compound of formula I (2-oxo acid), pyruvate (cosubstrate) is used which is reduced to lactate by means of a lactate dehydrogenase, which means that, in the regeneration reaction which reconverts the reduced cofactor into its original oxidized form, pyruvate is reduced to lactate by means of a lactate dehydrogenase.

In a preferred embodiment of the present invention, a process according to the present invention is characterized in that, as a compound of formula II (secondary alcohol), 2-propanol (isopropyl alcohol, IPA) (cosubstrate) is used which is oxidized to acetone by means of an alcohol dehydrogenase, which means that, in the regeneration reaction which reconverts the oxidized cofactor into its original reduced form, 2-propanol is oxidized to acetone by means of an alcohol dehydrogenase.

In a preferred embodiment of the present invention, a process according to the present invention is characterized in that oxygen is used which is reduced by means of an NADH oxidase.

In a preferred embodiment of the present invention, a process according to the present invention is characterized in that, as a secondary alcohol, malate (cosubstrate) is used which is oxidized to pyruvate and $CO_2$ by means of an oxaloacetate-decarboxylating malate dehydrogenase ("malate enzyme"), e.g., that in the regeneration reaction which reconverts the oxidized cofactor into its original reduced form, malate is oxidized to pyruvate and $CO_2$ by means of a malate dehydrogenase.

In this embodiment, the nascent pyruvate is reacted in a further redox reaction which does not serve for the formation of a product, but constitutes the second cofactor regeneration reaction.

In a preferred embodiment of the present invention, a process according to the present invention is characterized in that it is used for performing at least one oxidation reaction and at least one reduction reaction, respectively, in the same reaction batch on compounds of general formula

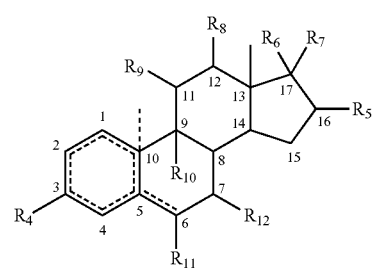

III wherein $R_4$ denotes hydrogen, a methyl group, a hydroxy group or an oxo group, $R_5$ denotes hydrogen, a hydroxy group, an oxo group or a methyl group, $R_6$ denotes hydrogen or a hydroxy group, $R_7$ denotes hydrogen, $—COR_{13}$, wherein $R_{13}$ is a $C_1$-$C_4$ alkyl group which is unsubstituted or substituted with a hydroxy group, or a $C_1$-$C_4$ carboxy alkyl group which is substituted, in particular with a hydroxy group, or unsubstituted, or $R_6$ and $R_7$ together denote an oxo group, $R_8$ denotes hydrogen, a methyl group, a hydroxy group or an oxo group, $R_9$ denotes hydrogen, a methyl group, a hydroxy group or an oxo group, $R_{10}$ denotes hydrogen, a methyl group or a halogen, $R_{11}$ denotes hydrogen, a methyl group, a hydroxy group, an oxo group or halogen, and $R_{12}$ denotes hydrogen, a hydroxy group, an oxo group or a methyl group, wherein the structural element

denotes a benzene ring or a ring comprising 6 carbon atoms and 0, 1 or 2 C—C-double bonds;

wherein the substrate(s) is/are preferably provided at a concentration of <5% (w/v) in the reaction batch for the reduction reaction(s) involved in the formation of the product.

In a preferred embodiment of the present invention, a process according to the present invention is characterized in that an enzymatic conversion of dehydroepiandrosterone (DHEA) of formula

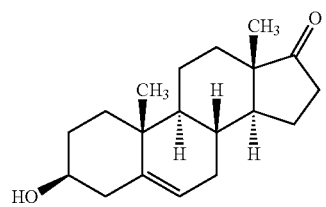

VII into testosterone of formula

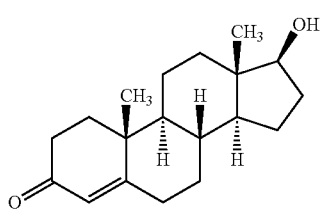

VIII takes place.

In a preferred embodiment of the present invention, a process according to the present invention is characterized in that an enzymatic epimerization of the hydroxysteroid compound 3α,7α-dihydroxy-5β-cholanic acid (chenodeoxycholic acid, CDC) of formula

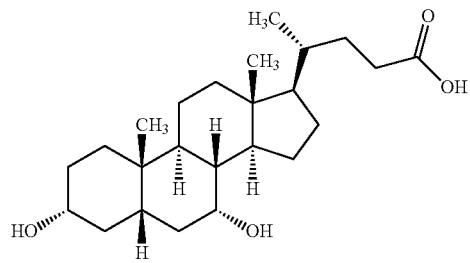

IV occurs via oxidation to ketolithocholic acid (KLC) of formula

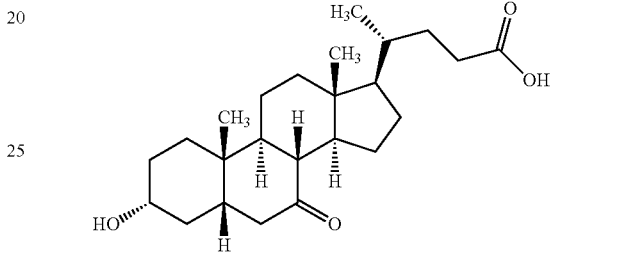

V and reduction to 3α,7β-dihydroxy-5β-cholanic acid (ursodeoxycholic acid, UDC) of formula

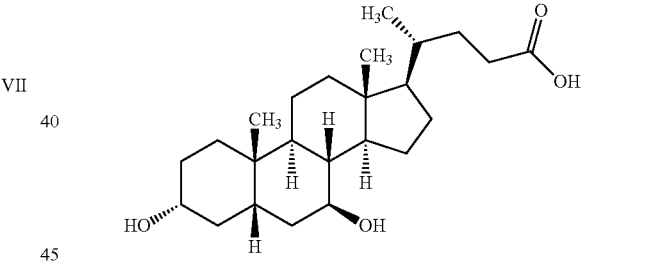

VI e.g. using two opposite stereospecific hydroxysteroid dehydrogenases.

In a preferred embodiment of the present invention, a process according to the present invention is characterized in that it is used for the enzymatic epimerization of 3α,7α,12α-trihydroxy-5β-cholanic acid (cholanic acid) of formula

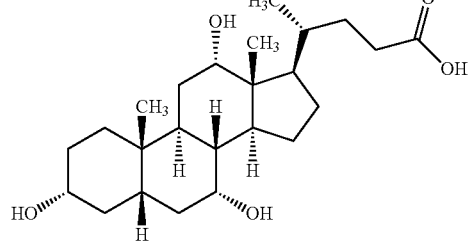

IX either
A) via oxidation to obtain 3α,7α-dihydroxy-12-oxo-5β-cholanic acid (12-oxo-CDC) of formula

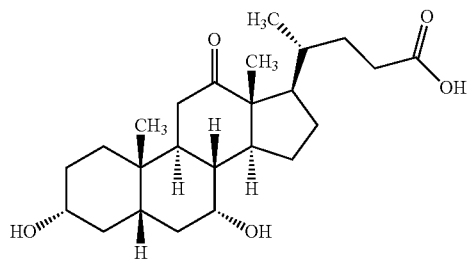

X which is further reacted to obtain 3α-hydroxy-7,12-dioxo-5β-cholanic acid (12oxo-KLC) of formula

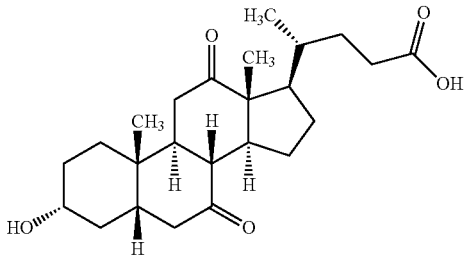

XI and subsequent reduction to the stereoisomeric hydroxy compound 3α,7β-dihydroxy-12-oxo-5β-cholanic acid (12-keto-ursodeoxycholanic acid) of formula

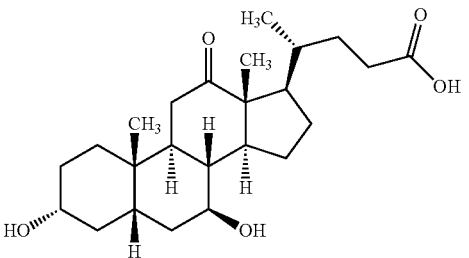

XII or
B) via oxidation to obtain 3α,12α-dihydroxy-7-oxo-5β-cholanic acid of formula

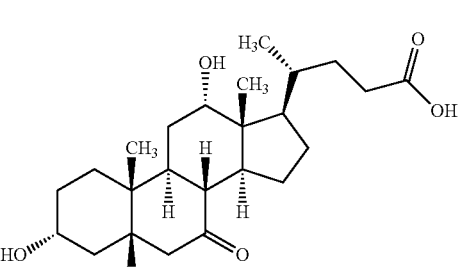

XIII followed by enzymatic oxidation to obtain 3α-hydroxy-7,12-dioxo-5β-cholanic acid(12oxo-KLC) of formula XI, and subsequent reduction to obtain the stereoisomeric hydroxy compound 3α,7β-dihydroxy-12-oxo-5β-cholanic acid (12-keto-ursodeoxycholanic acid) of formula XII,
or
C) via oxidation to obtain 3α,12α-dihydroxy-7-oxo-5β-cholanic acid of formula XIII, followed by enzymatic reduction to obtain 3α,7β,12α-triydroxy-5β-cholanic acid of formula

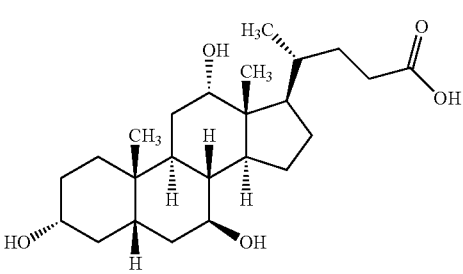

XIV and subsequent oxidation to obtain the stereoisomeric hydroxy compound 3α,7β-dihydroxy-12-oxo-5β-cholanic acid (12-keto-ursodeoxycholanic acid) of formula XII;
or
in any combination from A), B) and/or C)
e.g. using 3 stereospecific hydroxysteroid dehydrogenases, 2 of which have opposite stereospecifity.

In a preferred embodiment of the present invention, a process according to the present invention is characterized in that a $C_5$- or $C_6$-sugar is used as a substrate, e.g., that the process is used for the isomerization of $C_5$- or $C_6$-sugars.

In a preferred embodiment of the present invention, a process according to the present invention is characterized in that an isomerization of glucose occurs via reduction to sorbitol and oxidation to fructose, e.g., that the process is used for the isomerization of glucose via reduction to sorbitol and subsequent oxidation to fructose.

A process according to the present invention is preferably carried out in an aqueous system, wherein it is possible that the substrate for the oxidation and reduction reaction is partly provided in an undissolved state in the form of a suspension and/or as a second liquid phase.

In a particular embodiment, a process according to the present invention is characterized in that the substrate(s) for the oxidation reaction(s) involved in the formation of a product is/are provided in the reaction batch at a concentration of at least 5% (w/v) and more, preferably 7% (w/v) and more, particularly preferably 9% (w/v) and more, e.g. 5% (w/v) to 20% (w/v), such as 5% (w/v) to 15% (w/v), e.g. 5% (w/v) to 12% (w/v), such as 5% (w/v) to 10% (w/v).

According to a preferred embodiment of the process according to the invention, the substrate(s), which substrate(s) are used as substrate(s) of the product-forming reactions, are initially present in the reaction batch at a concentration of ≥3% (w/v).

In a particular embodiment, a process according to the present invention is characterized in that, on the whole, a turnover of ≥70%, in particular ≥90%, is achieved in the product-forming reactions.

In a process according to the present invention, a buffer can be added to the aqueous system. Suitable buffers are, for example, potassium phosphate, Tris-HCl and glycine with a pH ranging from 5 to 10, preferably from 6 to 9. Furthermore or alternatively, ions for stabilizing the enzymes, such as $Mg^{2+}$ or other additives such as glycerol, can be added to the system. In a process according to the present invention, the concentration of the added cofactors $NAD(P)^+$ and NAD(P)H is usually between 0.001 mM and 10 mM, preferably between 0.01 mM and 1 mM.

Depending on the enzymes used, the process according to the present invention can be performed at a temperature ranging from 10° C. to 70° C., preferably from 20° C. to 45° C.

Hydroxysteroid dehydrogenases (HSDH) are understood to be enzymes which catalyze the oxidation of hydroxy groups to the corresponding keto groups or, conversely, the reduction of keto groups to the corresponding hydroxy groups at the steroid skeleton.

Appropriate hydroxysteroid dehydrogenases which can be used for redox reactions on hydroxysteroids are, for example, 3α-HSDH, 3β-HSDH, 7α-HSDH, 7β-HSDH or 17β-HSDH.

Appropriate enzymes with 7α-HSDH activity can be obtained, for example, from Clostridia (*Clostridium absonum, Clostridium sordelii*), *Escherichia coli* or *Bacteroides fragilis*.

Appropriate enzymes with 7β-HSDH activity can be obtained, for example, from *Ruminococcus* sp. or *Clostridium absonum*.

Appropriate lactate dehydrogenases can be obtained, for example, from *Oryctolagus cuniculus*.

Appropriate alcohol dehydrogenases can be obtained, for example, from *Lactobacillus kefir*.

An appropriate xylose reductase can be obtained, for example, from *Candida tropicalis*.

Appropriate sorbitol dehydrogenases can be obtained, for example, from sheep liver, *Bacillus subtilis* or *Malus domestica*.

Appropriate NADH oxidases can be obtained, for example, from *Leuconostoc mesenteroides, Streptococcus mutans, Clostridium aminovalericum*.

In a process according to the present invention, enzymes are preferably used as proteins recombinantly overexpressed in *E. coli*, wherein the corresponding cell lysates preferably continue to be used without any further purification. Thereby, the enzyme unit 1 U corresponds to the enzyme amount which is required for reacting 1 μmol of substrate per min.

EXAMPLES

In the following examples, all temperature data are given in degrees Celsius (° C.). The following abbreviations are used:
EtOAc=ethyl acetate
h=hour(s)
IPA=isopropyl alcohol (2-propanol)
MeOH=methanol
Rt=room temperature Example 1

Epimerization of Chenodeoxycholic Acid into Ursodeoxycholic Acid by 7α-hydroxysteroid Dehydrogenase and 7β-hydroxysteroid Dehydrogenase, Using a Lactate Dehydrogenase- and Alcohol Dehydrogenase-Dependent Cofactor Regeneration System A 0.5 ml charge contains 50 mg chenodeoxycholic acid, 12 U of recombinant 7α-hydroxysteroid dehydrogenase from *Escherichia coli*, 6 U of recombinant 7β-hydroxysteroid dehydrogenase from *Ruminococcus torques* as well as 0.5 mM $NAD^+$ and 0.3 mM NADPH. For the regeneration of $NAD^+$, 6 U of recombinant lactate dehydrogenase and 350 mM sodium pyruvate are used. For the regeneration of NADPH, 6 U of recombinant alcohol dehydrogenase from *Lactobacillus kefir* and initially 2.4% IPA (w/v) are used. The reaction is performed in an aqueous potassium phosphate buffer (100 mM, pH=7.8) at 25° C., with continuous shaking (850 rpm). An open system continues to be used in order to facilitate the evaporation of acetone and to shift the reaction toward ursodeoxycholic acid. 1.6% (w/v) IPA is additionally dosed in after 6 h, 2.4% (w/v) IPA after 16 h, 3.9% (w/v) IPA after 24 h and 0.8% (w/v) IPA after 40 h. In addition, 20 μl of 4-methyl-2-pentanol is added after 24 h. 200 μl of 2-pentanol as well as 1.6% (w/v) IPA are added after 46 h. After 48 h, the proportion of ursodeoxycholic acid in all bile acids in the reaction mixture is >97%.

Example 2

Epimerization of Chenodeoxycholic Acid into Ursodeoxycholic Acid by 7α-hydroxysteroid Dehydrogenase and 7β-hydroxysteroid Dehydrogenase, Using a Lactate Dehydrogenase- and Malate Dehydrogenase-Dependent Cofactor Regeneration System A 0.5 ml charge contains 50 mg chenodeoxycholic acid, 20 U of recombinant 7α-hydroxysteroid dehydrogenase from *Escherichia coli*, 20 U of recombinant 7β-hydroxysteroid dehydrogenase from *Ruminococcus torques* as well as 1 mM $NAD^+$ and 1 mM NADPH. For the regeneration of $NAD^+$, 10 U of the lactate dehydrogenase (Sigma-Aldrich) are used, and for starting the reaction, 16.5 mM sodium pyruvate is used. For the regeneration of NADPH, 20 U of recombinant malate dehydrogenase from *Escherichia coli* and 320 mM sodium malate are used. The reaction is performed in an aqueous potassium phosphate buffer (100 mM, pH=7.8) at 25° C., with continuous shaking (850 rpm). An open system continues to be used in order to allow the nascent $CO_2$ to escape. 20 U of 7α-HSDH as well as 10 U of lactate dehydrogenase were additionally dosed in after 16 h and after 40 h. 10 U 7β-HSDH were additionally dosed in after 20 h, 24 h, 44 h and 48 h. Furthermore, 10 U of malate dehydrogenase were additionally dosed in after 40 h. After 72 h, the proportion of ursodeoxycholic acid in all bile acids in the reaction mixture is approximately 90%.

Example 3

Epimerization of Chenodeoxycholic Acid into Ursodeoxycholic Acid by 7α-hydroxysteroid Dehydrogenase and 7β-hydroxysteroid Dehydrogenase, Using an NADH Oxidase- and Alcohol Dehydrogenase-Dependent Cofactor Regeneration System A 0.5 ml charge contains 50 mg chenodeoxycholic acid, 12 U of recombinant 7α-hydroxysteroid dehydrogenase from *Escherichia coli*, 7.5 U of recombinant 7β-hydroxysteroid dehydrogenase from *Ruminococcus torques* as well as 1 mM $NAD^+$ and 1 mM NADPH. For the regeneration of $NAD^+$, 20 U of recombinant NADH oxidase from *Clostridium aminovalericum* are used. For the regeneration of NADPH, 5 U of recombinant alcohol dehydrogenase from *Lactobacillus kefir* and initially 2% IPA (w/v) are used.

The reaction is performed in an aqueous potassium phosphate buffer (100 mM, pH 6) at 25° C., with continuous shaking (850 rpm). An open system continues to be used in order to facilitate the evaporation of acetone and to shift the reaction toward ursodeoxycholic acid. 2% IPA is additionally dosed in after 18 h, 22 h, 26 h and 41 h as well as 5% IPA after 41 h and after 48 h. 20 U of NADH oxidase are additionally dosed in after 24 h, and 7.5 U of 7β-hydroxysteroid dehydrogenase as well as 5 U of alcohol dehydrogenase are additionally dosed in after 41 h. After 48 h, the proportion of ursodeoxycholic acid in all bile acids in the reaction mixture is approximately 95-98%.

Example 4

Reprocessing and Analytics of Bile Acids

Upon completion of reactions as described in Examples 1 to 3, the reaction mixture is extracted with EtOAc. Subsequently, the solvent is removed by evaporation. The evaporation residue is dissolved in a mixture of MeOH:acetonitrile:sodium phosphate buffer pH=3, 0.78 g/l (40:30:37) and the conversion of chenodeoxycholic acid into ursodeoxycholic acid is monitored by HPLC. Thereby, a reversed-phase separation column (ZORBAX®Eclipse® XDB C18, flow 0.8 ml/min) and a light-refraction detector (RID), Agilent 1260 Infinity®, both from Agilent Technologies Inc., are used.

Example 5

Conversion of Glucose into Fructose Via a Xylose Reductase and a Sorbitol Dehydrogenase, Using an Alcohol Dehydrogenase for Recycling the NADPH and a Lactate Dehydrogenase for Recycling the NAD⁺

A 0.5 ml charge contains 50 mg/ml glucose and 6 U/ml of recombinant xylose reductase from *Candida tropicalis* (overexpressed in *E. coli* BL21 (DE3)) and 0.1 mM NADP⁺. For the regeneration of the cofactor, 7% IPA and the recombinant alcohol dehydrogenase from *Lactobacillus kefir* (overexpressed in *E. coli* BL21 (DE3)) are added. The enzymes are used in the form of cell lysates. The reaction takes place for 24 h at 40° C. and pH=9 (50 mM Tris HCl-buffer) in an open system, with continuous shaking (900 rpm). The open system leads to the removal of acetone, which drives the reaction toward the formation of sorbitol. In the open system, water and IPA evaporate too, so that they are additionally dosed in after 6 h and after 21 h. Thereby at each time a total volume of 0.5 ml as well as an IPA concentration of 7% (v/v) is adjusted. After 24 h, the reaction vessel is incubated at 60° C. under vacuum in order to inactivate the enzymes and to evaporate the organic solvents. After cooling to room temperature, the recombinant sorbitol dehydrogenase from *Bacillus subtilis* (overexpressed in *E. coli* BL21 (DE3)) is added at a final concentration of 5 U/ml, $ZnCl_2$ at a final concentration of 1 mM and $NAD^+$ at a final concentration of 0.1 mM. For cofactor regeneration, 5 U/ml (final concentration) of lactate dehydrogenase from rabbit muscles (Sigma Aldrich) and 300 mM pyruvate are used. The charge is topped up to 0.5 ml with water. The reaction takes place for further 24 h at 40° C. in a closed system with continuous shaking (900 rpm). A conversion of D-glucose zu D-fructose of >90% is achieved.

Example 6

Conversion of Glucose into Fructose Via a Xylose Reductase and a Sorbitol Dehydrogenase, Using an Alcohol Dehydrogenase for Recycling the NADPH and a NADH Oxidase for Recycling the NAD⁺

A 0.5 ml charge contains 50 mg/ml glucose, 6 U/ml of recombinant xylose reductase from *Candida tropicalis* (overexpressed in *E. coli* BL21 (DE3)) and 0.1 mM NADP⁺. For the regeneration of the cofactor, 7% (v/v) IPA and the recombinant alcohol dehydrogenase from *Lactobacillus kefir* (overexpressed in *E. coli* BL21 (DE3)) are added. The enzymes are used in the form of cell lysates. The reaction takes place for 24 h at 40° C. and pH=8 (50 mM Tris HCl buffer) in an open system, with continuous shaking (900 rpm). The open system leads to the removal of acetone, which drives the reaction toward the formation of sorbitol. In the open system, water and IPA evaporate too, so that they are additionally dosed in after 6 h and after 21 h. Thereby at each time a total volume of 0.5 ml as well as an IPA-concentration of 7% (v/v) are adjusted. After 24 h, the reaction vessel is incubated at 60° C. under vacuum in order to inactivate the enzymes and to evaporate IPA as well as any acetone that has formed. After cooling to room temperature, the recombinant D-sorbitol dehydrogenase from *Bacillus subtilis* (overexpressed in *E. coli* BL21 (DE3)) is added at a final concentration of 5 U/ml, $CaCl_2$ at a final concentration of 1 mM and a mixture of $NAD^+$ and NADH at a final concentration of 0.1 mM. For cofactor regeneration, 10 U/ml (final concentration) of NADH oxidase from *Leuconostoc mesenteroides* (overexpressed in *E. coli* BL21 (DE3)) are used. The enzymes are used in the form of cell lysates. The charge is topped up to 0.5 ml with water. The reaction takes place for 24 h at 40° C. in an open system, with continuous shaking (900 rpm), in order to ensure sufficient oxygen supply for the NADH oxidase from the air. In that open system at 40° C. water evaporates. Thus, after 6 h and after 21 h it is filled up to with water to a volume of 0.5 ml. A conversion of D-glucose into D-fructose of ca. 98% is achieved.

Example 7

Reprocessing and Analytics of Sugars

The charge is incubated at 65° C. for 10 min for inactivating the enzymes and is subsequently centrifuged. The supernatant is then filtered over a 0.2 μM PVDF filter and analyzed by ligand-exchange HPLC (Agilent Technologies Inc.). In doing so, sugars and polyols are separated via a lead column of Showa Denko K.K. (Shodex® Sugar SP0810) with a flow of 0.5 ml/min water (VWR International GmbH, HPLC Grade) at 80° C. Detection occurs with the aid of a light-refraction detector (RID, Agilent 1260 Infinity®, Agilent Technologies Inc.). An inline filter of Agilent Technologies Inc. and, as precolumns, an anion-exchange column (Shodex® Axpak-WAG), a reversed-phase column (Shodex® Asahipak® ODP-50 6E) and a sugar precolumn (SUGAR SP-G) of Showa Denko K.K. are used.

Example 8

Bioconversion of Cholanic Acid to 3α,7-dihydroxy-12-oxo-5-cholanic Acid by 12α-hydroxysteroiddehydrogenase, 7α-hydroxysteroiddehydrogenase and 7β-hydroxysteroiddehydrogenase Using a Lactate Dehydrogenase and an Alcohol Dehydrogenase Dependent Cofactor Regeneration System A 0.5 ml charge contains 25 mg of cholanic acid 12.5 U of recombinant 12α-hydroxysteroid dehydrogenase from *Eggertella lenta* or *Lysinibacillus sphaericus*, 16 U of recombinant 7α-hydroxysteroid dehydrogenase from *Escherichia coli*, 6 U of recombinant 7β-hydroxysteroid dehydrogenase from *Ruminococcus torques*, as well as 1 mM NAD$^+$ and 1 mM NADPH. For regeneration of NAD$^+$ 12.5 U of recombinant lactate dehydrogenase from *Oryctolagus cuniculus* (muscle isoform) and 200 mM of sodium pyruvate are used. For regeneration of NADPH 5 U of recombinant alcohol dehydrogenase from *Lactobacillus kefir* and initially 2% of IPA (w/v) are used. The reaction is carried out in an aqueous potassium phosphate buffer (100 mM, pH 7.8) at 25° C. under continuous shaking (850 rpm). An open system is further used in order to allow evaporation of acetone and to shift the reaction towards 3α,7β-dihydroxy-12-oxo-5β-cholanic acid. After 18 h and 24 h 2% IPA (w/v) are dosed in additionally. After 48 h 61% of the cholanic acid used are reacted to 3α,7α-dihydroxy-12-oxo-5β-cholanic acid.

Example 9

Bioconversion of Cholanic Acid to 3α,7-dihydroxy-12-oxo-5-cholanic Acid by 12α-hydroxysteroid Dehydrogenase, 7α-hydroxysteroid Dehydrogenase and 7β-hydroxysteroid Dehydrogenase Using a Lactate Dehydrogenase, NADH-Oxidase and Alcohol Dehydrogenase Dependent Cofactor Regeneration System A 0.5 ml charge contains 25 mg of cholanic acid, 12.5 U of recombinant 12α-hydroxysteroid dehydrogenase from *Eggertella lenta* or *Lysinibacillus sphaericus*, 16 U of recombinant 7α-hydroxysteroid dehydrogenase from *Escherichia coli*, 6 U of recombinant 7β-hydroxysteroid dehydrogenase from *Ruminococcus torques*, as well as 1 mM NAD$^+$ and 1 mM NADPH. For the regeneration of NAD$^+$ 5 U of recombinant NADH oxidase from *Leuconostoc mesenteroides* and 12.5 U of recombinant lactate dehydrogenase from *Oryctolagus cuniculus* (muscle isoform) and 200 mM of sodium pyruvate are used. For the regeneration of NADPH 5 U of recombinant alcohol dehydrogenase from *Lactobacillus kefir* and initially 2% of IPA (w/v) are used. The reaction is carried out in an aqueous potassium phosphate buffer (100 mM, pH 7.8) at 25° C. under continuous shaking (850 rpm).

An open system is further used in order to allow evaporation of acetone and to shift the reaction towards 3α,7β-dihydroxy-12-oxo-5β-cholanic acid. After 18 h and 24 h 2% of IPA (w/v) are dosed in additionally. After 48 h 70% of the cholanic acid used are reacted to 3α,7α-dihydroxy-12-oxo-5β-cholanic acid.

Example 10

Epimerization of Chenodeoxy Cholanic Acid into Ursodeoxy Cholanic Acid Using 7α-hydroxysteroid Dehydrogenase and 7β-hydroxysteroid Dehydrogenase Under Use of a Lactate Dehydrogenase and Alcohol Dehydrogenase Dependent Cofactor Regeneration System. Advantage of Adding Manganese Chlorid (MnCl$_2$)

A 0.5 ml charge contains 50 mg of chenodeoxy cholanic acid, 12 U of recombinant 7α-hydroxysteroiddehydrogenase aus *Escherichia coli*, 6 U of the recombinant 7β-hydroxysteroid dehydrogenase from *Ruminococcus torques*, as well as 0.5 mM NAD$^+$ and 0.3 mM NADPH. For the regeneration of NAD$^+$ 6 U of recombinant lactate dehydrogenase and 350 mM of sodium pyruvate are used. For the regeneration of NADPH 6 U of recombinant alcohol dehydrogenase from *Lactobacillus kefir* and initially 2.4% of IPA (w/v) are used. The reaction is carried out in an aqueous potassium phosphate buffer (100 mM, pH=7.8) with 5 mM MnCl$_2$ at 25° C. and under continuous shaking (850 rpm). An open system is further used in order to allow evaporation of acetone and to shift the reaction towards ursodeoxy cholanic acid. 1.6% (w/v) of IPA after 6 h, 2.4% (w/v) of IPA after 16 h and 3.9% (w/v) of IPA after 24 h are dosed in additionally. After 36 h 200 µl of 2-pentanol as well as 3% (w/v) of IPA are added and after 48 h 100 µl 2-pentanol and 4% (w/v) of IPA are dosed in additionally. After 64 h the part of ursodeoxy cholanic acid of all bile acids in the reaction mixture is >99%. In particular, the part of chenodeoxy cholanic acid ca. 0.3%. In a control charge without the addition of MnCl$_2$ the part of chenodeoxy cholanic acid is at ca. 2% and the part of ursodeoxy cholanic acid at ca. 97.5% (average value from 5 experiments each).

Example 11

Epimerization of chenodeoxy cholanic acid to ursodeoxy cholanic acid by 7α-hydroxysteroid dehydrogenase and 7β-hydroxysteroid dehydrogenase under use of an alcohol dehydrogenase dependent cofactor regeneration system as well as a combined lactate dehydrogenase and NADH oxidase dependent cofactor regeneration system A 0.5 ml charge contains 50 mg of chenodeoxy cholanic acid, 12 U of recombinant 7α-hydroxysteroid dehydrogenase from *Escherichia coli*, 6 U of recombinant 7β-hydroxysteroid dehydrogenase from *Ruminococcus torques*, as well as 0.5 mM of NAD$^+$ and 0.3 mM of NADPH. For the regeneration of NAD$^+$ 6 U of recombinant lactate dehydrogenase and 350 mM of sodium pyruvate are used. For the regeneration of NAD$^+$ in addition 9 U of recombinant NADH oxidase from *Leuconostoc mesenteroides*, as well as 6 U of recombinant NADH oxidase from *Clostridium aminovalericum* are used. For the regeneration of NADPH 6 U of recombinant alcohol dehydrogenase from *Lactobacillus kefir* and initially 2.4% (w/v) of IPA are used. The reaction is carried out in an aqueous potassium phosphate buffer (100 mM, pH=7.8) at 25° C. under continuous shaking (850 rpm). An open system is further used in order to allow evaporation of acetone and to shift the reaction towards ursodeoxy cholanic acid. After 6 h 1.6% (w/v) of IPA, after 16 h 2.4% (w/v) of IPA and after 24 h 3.9% (w/v) of IPA are dosed in additionally. After 36 h 200 µl of 2-pentanol as well as 3% (w/v) of IPA are added and after 48 h 100 µl of 2-pentanol and 4% (w/v) of IPA are additionally dosed in. After 64 h the part of ursodeoxy cholanic acid of all bile acids in the reaction mixture is >99%. In particular the part of chenodeoxy cholanic acid is ca. 0.2%. In a control charge without addition of NADH-oxidase the part of chenodeoxy cholanic acid is at ca. 2% and the part of ursodeoxy cholanic acid at ca. 97.5% (same control charge as in example 11; average values from 5 experiments each).

Example 12

Epimerization of Chenodeoxy Cholanic Acid to Ursodeoxy Cholanic Acid by 7α-hydroxysteroid Dehydrogenase and 7β-hydroxysteroid Dehydrogenase Under Use of an Alcohol Dehydrogenase Dependent Cofactor Regeneration System as well as a Combined Lactate Dehydrogenase and NADH Oxidase Dependent Cofactor Regeneration System. Additive Effect of 2-pentanol and 2-propanol A 50 ml charge contains 5 g of chenodeoxy cholanic acid, 24 U/ml of recombinant 7α-hydroxysteroid dehydrogenase from *Escherichia coli*, 12 U/ml of recombinant 7β-hydroxysteroid dehydrogenase from *Ruminococcus torques* as well as 055 mM of $NAD^+$ and 0.3 mM of NADPH. For the regeneration of $NAD^+$ 12 U/ml recombinant lactate dehydrogenase and 350 mM of sodium pyruvate are used. For the regeneration of $NAD^+$ additionally 18 U/ml of recombinant NADH oxidase from *Leuconostoc mesenteroides* as well as 12 U/ml of recombinant NADH oxidase from *Clostridium aminovalericum* are used. For the regeneration of NADPH 12 U/ml of recombinant Alcohol dehydrogenase from *Lactobacillus kefir* and initially 1.5% (w/v) of IPA are used. The reaction is carried out in an aqueous potassium phosphate buffer (100 mM, pH=7.8) with 5 mM $MnCl_2$ at 25° C. In a 3-neck-piston it is stirred with a KPG-stirrer at ca. 100 rpm. Removal of acetone which originates from the reaction is effected by a stream of air (ca. 400-600 ml/min) through the reaction vessel. Since at the same time 2-propanol is evaporated as well, additional dosing is necessary, e.g. in an amount of 0.75 ml (1.5 h), 0.75 ml (3 h), 0.5 ml (4 h), 0.75 ml (6 h), 0.75 ml (8 h), 0.5 ml (11 h), 0.5 ml (14 h), 0.5 ml (17 h), 0.5 ml (21 h), 1 ml (23 h), 2.5 ml (25 h), 4 ml (29 h). After ca. 30 h, 20 ml 2-pentanol as well as 2 ml 2-propanol were added. After 46 h of total reaction time the part of 7-ketolithocholanic acid is ca. 1% (related to the sum of chenodeoxy cholanic acid, ursodeoxy cholanic acid and 7-ketolithocholanic acid. Further 2-propanol is added: 3 ml (46 h), 4 ml (52 h), 4 ml (54 h), as well as in addition 10 ml of 2-pentanol. After 72 h reaction time in total the part of 7-ketolithocholanic acid can be lowered to less than 0.2%. The part of ursodeoxy cholanic acid is >99%.

Example 13

Workup and Analytics of Bile Acids

After termination of the reaction as described in examples 8 to 12, the bile acids which are present in the trials may be analyzed via a method as described in example 4.

The invention claimed is:
1. A process for the enzymatic regeneration of the redox cofactors $NAD^+/NADH$ and $NADP^+/NADPH$ in a one-pot reaction, wherein, as a result of at least two further enzymatically catalysed redox reactions proceeding in the same reaction batch (product-forming reactions), the redox cofactor $^+/NADH$ accumulates in its reduced form as NADH and the redox cofactor $NADP^+/NADPH$ accumulates in its oxidized form as $NADP^+$, wherein:
   a) in the regeneration reaction which reconverts NADH into its original oxidized form, oxygen or pyruvate is reduced by means of an NADH oxidase or a lactate dehydrogenase, and
   b) in the regeneration reaction which reconverts $NADP^+$ into its original reduced form, 2-propanol or malate is oxidized by means of an alcohol dehydrogenase or a malate dehydrogenase.

2. The process according to claim 1, wherein oxidation reaction(s) and reduction reaction(s) take place on the same substrate (molecular backbone).

3. The process according to claim 1, wherein oxidation reaction(s) and reduction reaction(s) proceed chronologically parallel.

4. The process according to claim 1, wherein, in the regeneration reaction which reconverts NADP+ to NADPH, 2-propanol is oxidized to acetone by means of an alcohol dehydrogenase.

5. The process according to claim 1, wherein, in the regeneration reaction which reconverts NADH to NAD+, pyruvate is reduced to lactate by means of a lactate dehydrogenase.

6. The process according to claim 5, wherein, in the regeneration reaction which reconverts NADP+ to NADPH, malate is oxidized to pyruvate and $CO_2$ by means of a malate dehydrogenase.

7. The process according to claim 1, wherein the process is used for performing at least one oxidation reaction and at least one reduction reaction, respectively, in the same reaction batch on compounds of general formula

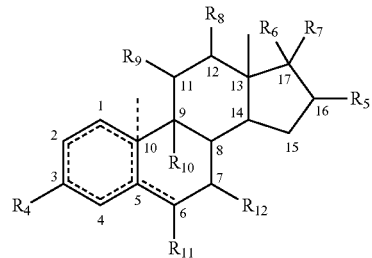

III wherein
   $R_4$ denotes hydrogen, a methyl group, a hydroxy group or an oxo group,
   $R_5$ denotes hydrogen, a hydroxy group, an oxo group or a methyl group,
   $R_6$ denotes hydrogen or a hydroxy group,
   $R_7$ denotes hydrogen, CORD, wherein $R_{13}$ is a $C_1$-$C_4$ alkyl group which is unsubstituted or substituted with a hydroxy group, or a $C_1$-$C_4$ carboxy alkyl group which is substituted or unsubstituted,
   or $R_6$ and $R_7$ together denote an oxo group,
   $R_8$ denotes hydrogen, a methyl group, a hydroxy group or an oxo group,
   $R_9$ denotes hydrogen, a methyl group, a hydroxy group or an oxo group,
   $R_{10}$ denotes hydrogen, a methyl group or halogen,
   $R_{11}$ denotes hydrogen, a methyl group, a hydroxy group, an oxo group or halogen, and R$_{12}$ denotes hydrogen, a hydroxy group, an oxo group or a methyl group,
wherein the structural element

denotes a benzene ring or a ring comprising 6 carbon atoms and 0, 1 or 2 C—C-double bonds.

8. The process according to claim 7, wherein R$_7$ denotes —COR$_{13}$, wherein R$_{13}$ is a C$_1$-C$_4$ carboxy alkyl group which is substituted with a hydroxy group.

9. The process according to claim 7, wherein it is used for the conversion of dehydroepiandrosterone of formula

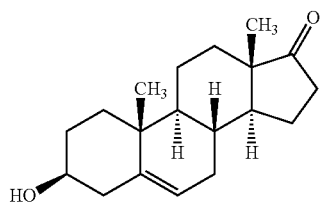

VII into testosterone of formula

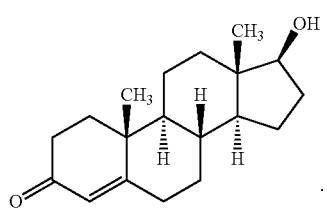

VIII

10. The process according to claim 7, wherein it is used for the enzymatic epimerization of 3α,7α-dihydroxy-5β-cholanic acid of formula

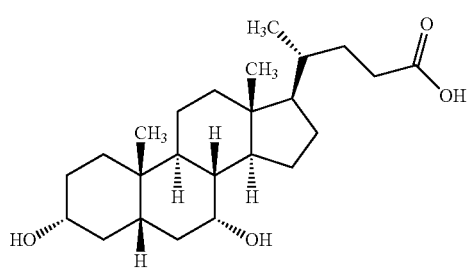

IV into ketolithocholic acid of formula

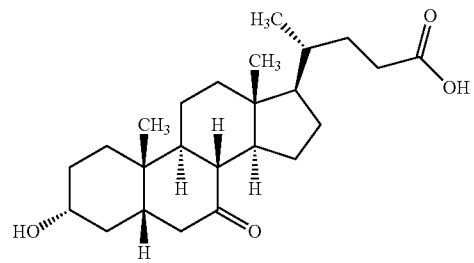

V by oxidation, and into the stereoisomeric hydroxy compound 3α,7β-dihydroxy-5β-cholanic acid of formula

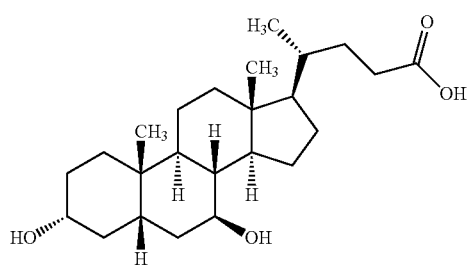

VI by subsequent reduction,
using two opposite stereospecific hydroxysteroid dehydrogenases.

11. The process according to claim 10, whereby the oxidation reaction is catalysed by a 7α-hydroxysteroid dehydrogenase from *E. coli*; and/or the reduction reaction is catalysed by a 7β-hydroxysteroid dehydrogenase from *Ruminococcus torques*.

12. The process according to claim 7, wherein it is used for the enzymatic epimerization of 3α,7α,12α-trihydroxy-5β-cholanic acid (cholanic acid) of formula

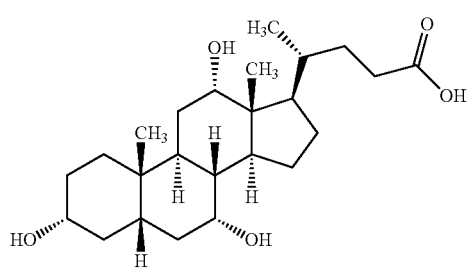

IX either

A) via oxidation to obtain 3α,7α-dihydroxy-12-oxo-5β-cholanic acid (12-oxo-CDC) of formula

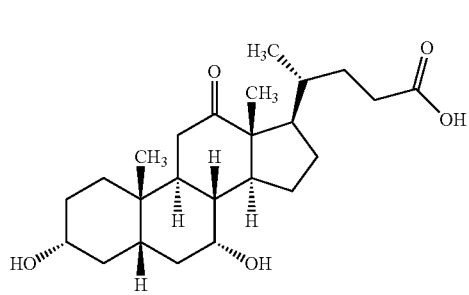

X which is further reacted to obtain 3α-hydroxy-7,12-dioxo-5β-cholanic acid (12oxo-KLC) of formula

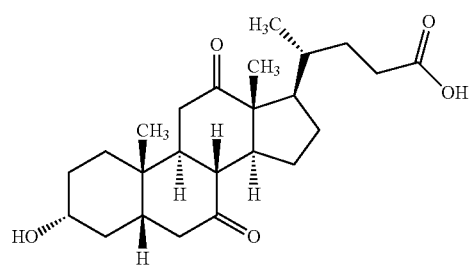

XI and subsequent reduction to the stereoisomeric hydroxy compound 3α,7β-dihydroxy-12-oxo-5β-cholanic acid (12-keto-ursodeoxycholanic acid) of formula

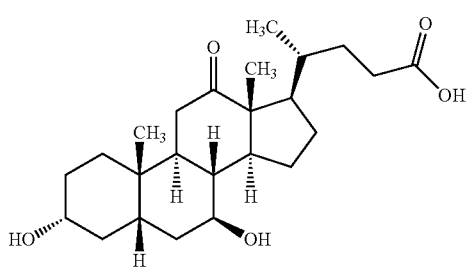

XII or

B) via oxidation to obtain 3α,12α-dihydroxy-7-oxo-5β-cholanic acid of formula

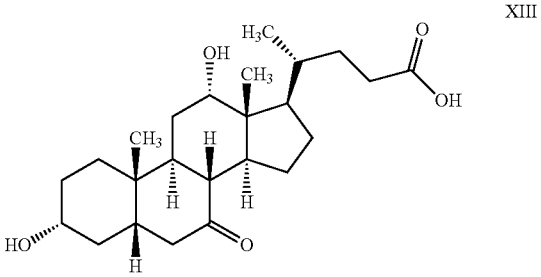

XIII followed by enzymatic oxidation to obtain 3α-hydroxy-7,12-dioxo-5β-cholanic acid (12oxo-KLC) of formula XI, and subsequent reduction to obtain the stereoisomeric hydroxy compound 3α,7β-dihydroxy-12-oxo-5β-cholanic acid (12-keto-ursodeoxycholanic acid) of formula XII, or C) via oxidation to obtain 3α,12α-dihydroxy-7-oxo-5β-cholanic acid of formula XIII, followed by enzymatic reduction to obtain 3α,7β,12α-trihydroxy-5β-cholanic acid of formula

XIV and subsequent oxidation to obtain the stereoisomeric hydroxy compound 3α,7β-dihydroxy-12-oxo-5β-cholanic acid (12-keto-ursodeoxycholanic acid) of formula XII;

using 3 stereospecific hydroxysteroid dehydrogenases, 2 of which have opposite stereospecificity.

13. The process according to claim 1, wherein it is used for the isomerization of $C_5$- or $C_6$-sugars.

14. The process according to claim 13 for the isomerization of glucose via reduction to sorbitol and subsequent oxidation to fructose.

15. The process according to claim 1, wherein the substrate(s) for the oxidation reaction(s) involved in the formation of a product is/are provided in the reaction batch at a concentration of at least 5% (w/v) and more.

16. The process according to claim 1, wherein, on the whole, a turnover of ≥70% is achieved in the two further enzymatically catalysed redox reactions proceeding in the same reaction batch.

17. The process according to claim 16, wherein, on the whole, a turnover of ≥90% is achieved in the two further enzymatically catalysed redox reactions proceeding in the same reaction batch.

* * * * *